US008859600B2

(12) United States Patent
Kiyota et al.

(10) Patent No.: US 8,859,600 B2
(45) Date of Patent: Oct. 14, 2014

(54) ACETONE SOLVATE CRYSTALS OF TRITYL OLMESARTAN MEDOXOMIL

(75) Inventors: Hiroshi Kiyota, Hiratsuka (JP); Hideaki Ishikawa, Hiratsuka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/266,967

(22) PCT Filed: Apr. 27, 2010

(86) PCT No.: PCT/JP2010/057404
§ 371 (c)(1),
(2), (4) Date: Nov. 8, 2011

(87) PCT Pub. No.: WO2010/126014
PCT Pub. Date: Nov. 4, 2010

(65) Prior Publication Data
US 2012/0059172 A1    Mar. 8, 2012

(30) Foreign Application Priority Data

Apr. 28, 2009    (JP) ................................ 2009-109160

(51) Int. Cl.
*A61K 31/4178* (2006.01)
*C07D 405/14* (2006.01)
*C07D 403/10* (2006.01)

(52) U.S. Cl.
CPC .......... *C07D 405/14* (2013.01); *A61K 31/4178* (2013.01); *C07D 403/10* (2013.01)
USPC .......................................... 514/382; 548/253

(58) Field of Classification Search
CPC .................................................... C07D 405/14
USPC .......................... 514/382; 548/250, 252, 253
See application file for complete search history.

(56) References Cited

U.S. PATENT DOCUMENTS

| | | | |
|---|---|---|---|
| 5,616,599 A | 4/1997 | Yanagisawa et al. | |
| 5,646,171 A | 7/1997 | Yanagisawa et al. | |
| 5,744,612 A | 4/1998 | Koguro et al. | |
| 6,040,454 A | 3/2000 | Koguro et al. | |
| 7,528,258 B2 * | 5/2009 | Hedvati et al. | 548/253 |
| 7,563,814 B2 * | 7/2009 | Hedvati et al. | 514/385 |
| 8,048,904 B2 * | 11/2011 | Ramanjaneyulu et al. | 514/382 |
| 8,076,492 B2 | 12/2011 | Pathi et al. | |
| 2006/0069141 A1 | 3/2006 | Hedvati et al. | |
| 2006/0074117 A1 * | 4/2006 | Hedvati et al. | 514/381 |
| 2006/0149078 A1 | 7/2006 | Hedvati et al. | |
| 2007/0054948 A1 | 3/2007 | Hedvati et al. | |
| 2008/0076932 A1 | 3/2008 | Razzetti et al. | |
| 2009/0281327 A1 | 11/2009 | Ramanjaneyulu et al. | |
| 2010/0076200 A1 | 3/2010 | Hedvati et al. | |
| 2011/0092713 A1 | 4/2011 | Sato et al. | |

FOREIGN PATENT DOCUMENTS

| | | |
|---|---|---|
| CN | 1976926 A | 6/2007 |
| CN | 1993355 A | 7/2007 |
| CN | 101094850 A | 12/2007 |
| CN | 101238119 A | 8/2008 |
| EP | 0796852 A1 | 9/1997 |
| EP | 0503785 B1 | 4/2001 |
| EP | 2036904 A1 | 3/2009 |
| JP | 7-121918 | 12/1995 |
| JP | 3521304 B2 | 4/2004 |
| JP | 3671266 B2 | 4/2004 |
| JP | 2004-217542 A | 8/2004 |
| JP | 2006-111586 A | 4/2006 |
| JP | 2007-509992 | 4/2007 |
| JP | 2007-509993 | 4/2007 |
| JP | 2007-526342 | 9/2007 |
| JP | 2008-088172 | 4/2008 |
| WO | WO 2006/029056 | 3/2006 |
| WO | WO 2006/029057 | 3/2006 |
| WO | WO 2006/073519 | 7/2006 |
| WO | 2007017135 A2 | 2/2007 |
| WO | WO 2007/047838 | 4/2007 |
| WO | WO 2007/048361 | 5/2007 |
| WO | WO 2007/148344 | 12/2007 |
| WO | WO 2008/043996 | 4/2008 |
| WO | WO 2009/019304 | 2/2009 |
| WO | WO 2010/026255 | 3/2010 |
| WO | WO 2011/014611 | 2/2011 |
| WO | WO 2012/001694 | 1/2012 |

OTHER PUBLICATIONS

Yanagisawa, H, "Nonpeptide Angiotensin II Receptor Antagonists: Synthesis, Biological Activities, and Structure-Activity Relationships of Imidazole-5-carboxylic Acids Bearing Alkyl, Alkenyl, and Hydroxyalkyl Substituents at the 4-Position and Their Related Compounds", J. Med. Chem., 39, 323-338 (1996).
Koike, H., "Olmesartan Medoxomil, a Novel Potent Angiotensin II Blocker", Annu. Rep. Sankyo Res. Lab. (Sankyo Kenkyusho Nempo) 55, 1-91 (2003).
International Preliminary Report on Patentability, issued in PCT/JP2010/057403, mailed Nov. 9, 2011.
International Search Report, issued in PCT/JP2010/057403, mailed Jun. 8, 2010.
Written Opinion of the International Searching Authority, issued in PCT/JP2010/057403, mailed Jun. 8, 2010.
International Preliminary Report on Patentability, issued in PCT/JP2010/057404, mailed Nov. 9, 2011.
International Search Report, issued in PCT/JP2010/057404, mailed Jun. 8, 2010.
Written Opinion of the International Searching Authority, issued in PCT/JP2010/057404, mailed Jun. 8, 2010.
U.S. Appl. No. 13/266,885, filed Nov. 17, 2011, Shigeo Yanagihara.
Office Action and Search Report issued in Chinese Application No. 2010800189009; dated Jul. 31, 2013.
Office Action and Search Report issued in Chinese Application No. 2010800188970; dated Aug. 12, 2013.

(Continued)

*Primary Examiner* — Michael Barker
(74) *Attorney, Agent, or Firm* — Locke Lord, LLP (57) ABSTRACT

Acetone solvate crystals of trityl olmesartan medoxomil are provided.

23 Claims, 7 Drawing Sheets

(56) References Cited

OTHER PUBLICATIONS

Office Action issued in Colombian Application No. 11161167; dated Aug. 28, 2013.
Vila Jato, J.L., Technologia Farmaceutica, vol. 1, pp. 42 to 49 (cited at pp. 3, 4 of English translation of Colombia opposition filed by Tecnoquimicas S.A., previously submitted) (1998).
Supplementary European Search Report, issued in EP Application No. 10769711.2, mailed Sep. 6, 2012.
Supplementary European Search Report, issued in EP Application No. 10769712.0, mailed Aug. 24, 2012.
English Translation of Opposition filed by Tecnoquimicas S.A., against Colombia App. No. 11-161167, Gazette 647, Publication No. 817, Jun. 29, 2012.
English Translation of Defense of Opposition by Tecnoquimicas S.A., against Colombia App. No. 11-161167, Gazette 647, Publication No. 817, Jun. 29, 2012.
English Translation of Opposition filed by Laboratorio Franco Colombiano S.A.S. Lafrancol S.A.S., against Colombia App. No. 11-161167, Gazette 647, Publication No. 817, Jun. 29, 2012.
Giron, D., Technochimica acta 248-1-59, Elsevier Science B.V., 1995, pp. 3 to 11.
J. Garrido, Form and Structure of Crystals, (op. cit.), chapter V, pp. 204, 212 (with English translation). (1973).
8-A.R. Verna, P. Krishna—"Polytypism in crystals", John Wiley and Son Inc., New York 1966.
Doelke E. Crystalline modifications and polymorphism changes during drug manufacture, Ann Pharm Fr. May 2002; 60(3): 161-76 (with English abstract).
The Merck Index. "An encyclopedia of chemicals, drugs, and biological. Fourteenth Edition." 2006. p. 1178. (Olmesartan).
EPO Third Party Observation, filed Sep. 21, 2012 against EPA No. 10769712.0.
International Preliminary Examination Report on Patentability for International Application No. PCT/JP2009/060419, corresponding to related U.S. Appl. No. 12/996,697, issued on Dec. 13, 2010 and the English translation issued on Jan. 11, 2011.
International Search Report for International Application No. PCT/JP2009/060419, corresponding to related U.S. Appl. No. 12/996,697, mailed on Aug. 11, 2009 (English & Japanese).
Written Opinion of the International Searching Authority for International Application No. PCT/JP2009/060419, corresponding to related U.S. Appl. No. 12/996,697, mailed on Aug. 11, 2009 (English & Japanese).

Marceau, P. et al. "Graphite intercalation compounds as precursors of activated metals. II *. Synthesis of beta, gamma-unsaturated ketones through condensation of allylic organozinc derivatives with nitriles." Journal of Organometallic Chemistry, 403:21-27 (1991).
Akiyama, Y. et al. "Reaction of organocadmium reagents with ethyl cyanoformate: preparation of alpha-keto esters." Chemistry Letters, 1231-1232 (1983).
Lee, A.S-Y., et al. "Synthesis of allyl ketone via Lewis acid promoted Barbier-type reaction." Tetrahedron Letters, 41:8803-8806 (2000).
EP Search Report for EP 09762446, corresponding to related U.S. Appl. No. 12/996,697, dated Aug. 29, 2011.
Khurana, J., et al. "A novel method of synthesis of 1,2-diketones from 1,2-diols using N-bromosuccinimide," Tetrahedron Letters, 44:4909-4912 (2003).
Grant, D.J.W., "Theory and Origin of Polymorphism", in HG Brittain (ed.) Polymorphism in Pharmaceutical Solids. Marcel Dekker, Inc., New York, Ch. 1, pp. 1-33, Jan. 1999.
Guillory, JK, "Generation of polymorphs, hydrates, solvates, and amorphous solids", in HG Brittain (ed.) Polymorphism in Pharmaceutical Solids. Marcel Dekker, Inc., New York, Ch. 5, pp. 183-226. Jan. 1999.
Caira, MR, "Crystalline Polymorphism of organic compound", Topics in Current Chemistry, Springer, Berlin, De., vol. 198, pp. 163-208, Jan. 1, 1998.
Byrn, S., "Pharmaceutical Solids: A Strategic Approach to Regulatory Considerations", Pharmaceutical Research, vol. 12(7), pp. 945-954, Jul. 1995.
Preparado Farmaceutoco Y Su Elaboracion, in Remington 2 Farmacia 17a edicion; Marino, M.A. (ed.); Editorial Medica Panamericana, S.A.; pp. 1912-1920 (Jul. 1987) (This is a Spanish-language document. Corresponding pages from the 19th Edition of the English-language reference is cited below).
Preformulation, in Remington: The Science and Practice of Pharmacy, Nineteenth Edition, vol. II; Gennaro, A.R. (ed.); Mack Publishing Company, Easton, PA; pp. 1451-1457 (Jun. 1995).
Information Statement submitted by anonymous 3rd-party in corresponding Japanese Application No. JP 2011-511396, reported from the JPO to the assignee on Jun. 4, 2014.
English translation of Information Statement submitted by anonymous 3rd-party in corresponding Japanese Application No. JP 2011-511396, reported from the JPO to the assignee on Jun. 4, 2014.

* cited by examiner

|  | Acetone content |
|---|---|
| Example 1 | 6.8% |
| Example 2 | 6.8% |
| Reference Example | 0.4% |

ACETONE SOLVATE CRYSTALS OF TRITYL OLMESARTAN MEDOXOMIL

This application is a national phase entry under 35 U.S.C. §371 of International Application Number PCT/JP2010/057404, filed on Apr. 27, 2010, entitled "NOVEL SOLVATE CRYSTALS", which claims the benefit of Japanese Patent Application Number JP 2009-109160, filed on Apr. 28, 2009, all of which are hereby incorporated by reference.

FIELD OF THE INVENTION

The present invention relates to novel solvate crystals.

BACKGROUND

Olmesartan medoxomil, which is an angiotensin II receptor antagonist, is useful as an active ingredient in medicaments for treatment and prophylaxis of hypertension (for example, Patent documents 1 to 5 and Non-patent documents 1 and 2).

Olmesartan medoxomil is produced from olmesartan with the steps described below, and it has been desired to obtain novel crystals of trityl olmesartan medoxomil, which is a precursor of the final product, in order to improve operability and achieve an efficient production of a high-purity final product.

Olmesartan

Trityl olmesartan medoxomil

Olmesartan medoxomil

Olmesartan medoxomil dehydrate

Tritylhalide (Tr—X)        DMDO halide (DMDO—X)

PRIOR ART DOCUMENTS

Patent Documents

Patent document 1: Japanese Examined Patent Publication No. Hei 7-121918 (Japanese Patent No. 2082519)
Patent document 2: U.S. Pat. No. 5,616,599
Patent document 3: International Patent Publication No. WO2006/029056
Patent document 4: International Patent Publication No. WO2006/029057
Patent document 5: International Patent Publication No. WO2006/073519

Non-Patent Documents

Non-patent document 1: J. Med. Chem., 39, 323-338 (1996)
Non-patent document 2: Annu. Rep. Sankyo Res. Lab. (Sankyo Kenkyusho Nempo) 55, 1-91 (2003)

SUMMARY OF THE INVENTION

Object of the Invention

It is an object of the present invention to provide novel acetone solvate crystals of trityl olmesartan medoxomil.

Means for Achieving the Object

As a result of much diligent research, the present inventors have found that acetone solvate crystals of trityl olmesartan medoxomil are precipitated by cooling the reaction product after tritylation and DMDO esterification steps in acetone containing water, and the present invention has been completed.

The present invention encompasses the following aspects (1) to (23).

(1) Acetone solvate crystals of trityl olmesartan medoxomil.

Figure 1:
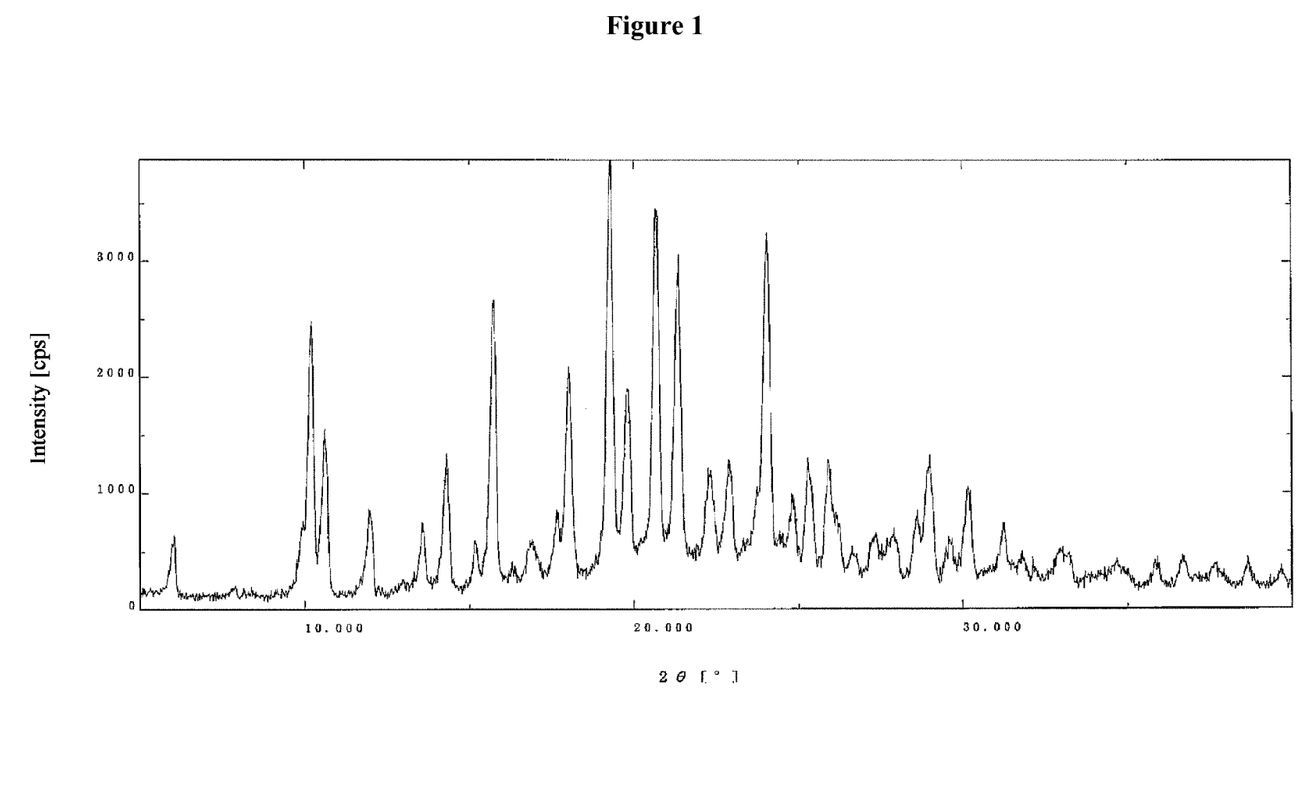
FIG. 1 shows an X-ray crystal diffraction pattern of the crystals obtained in Example 1.
Figure 2:
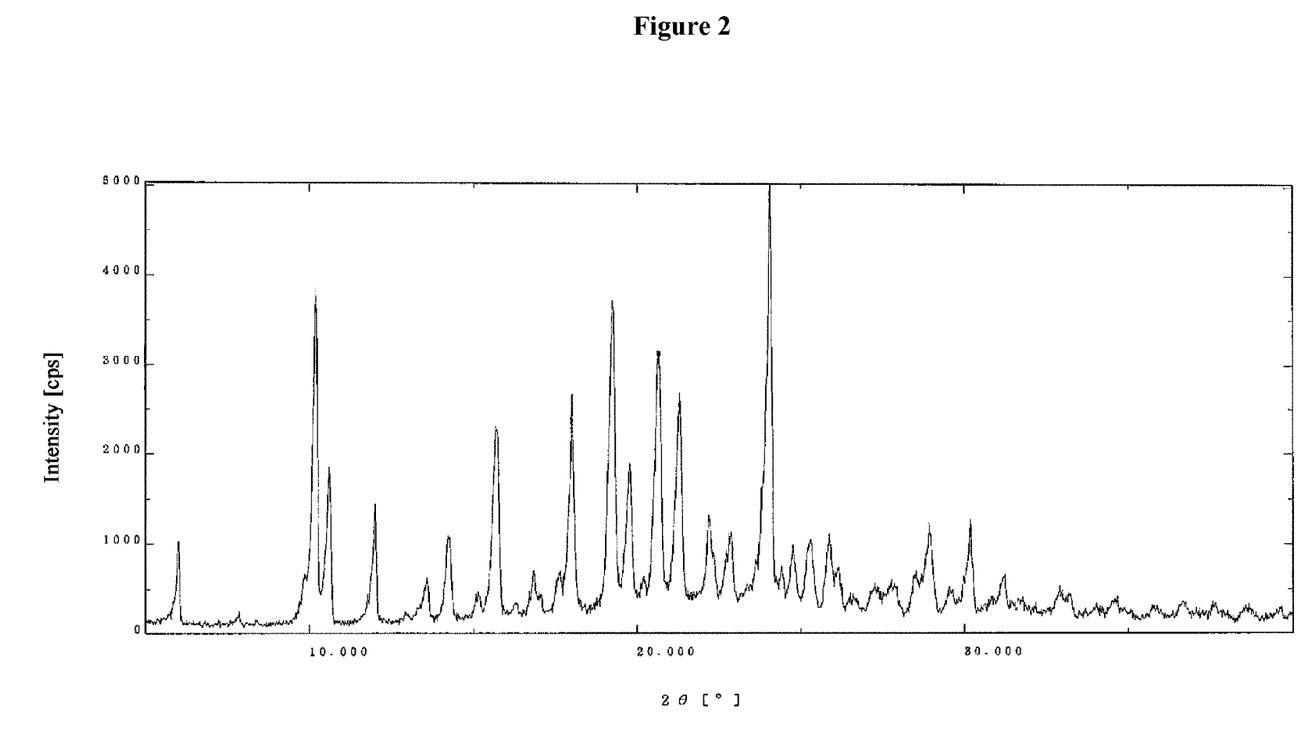
FIG. 2 shows an X-ray crystal diffraction pattern of the crystals obtained in Example 2.

(2) The crystals according to (1), which exhibit a pattern equivalent to FIG. 1 or FIG. 2 in powder X-ray crystal diffraction.

Figure 4:
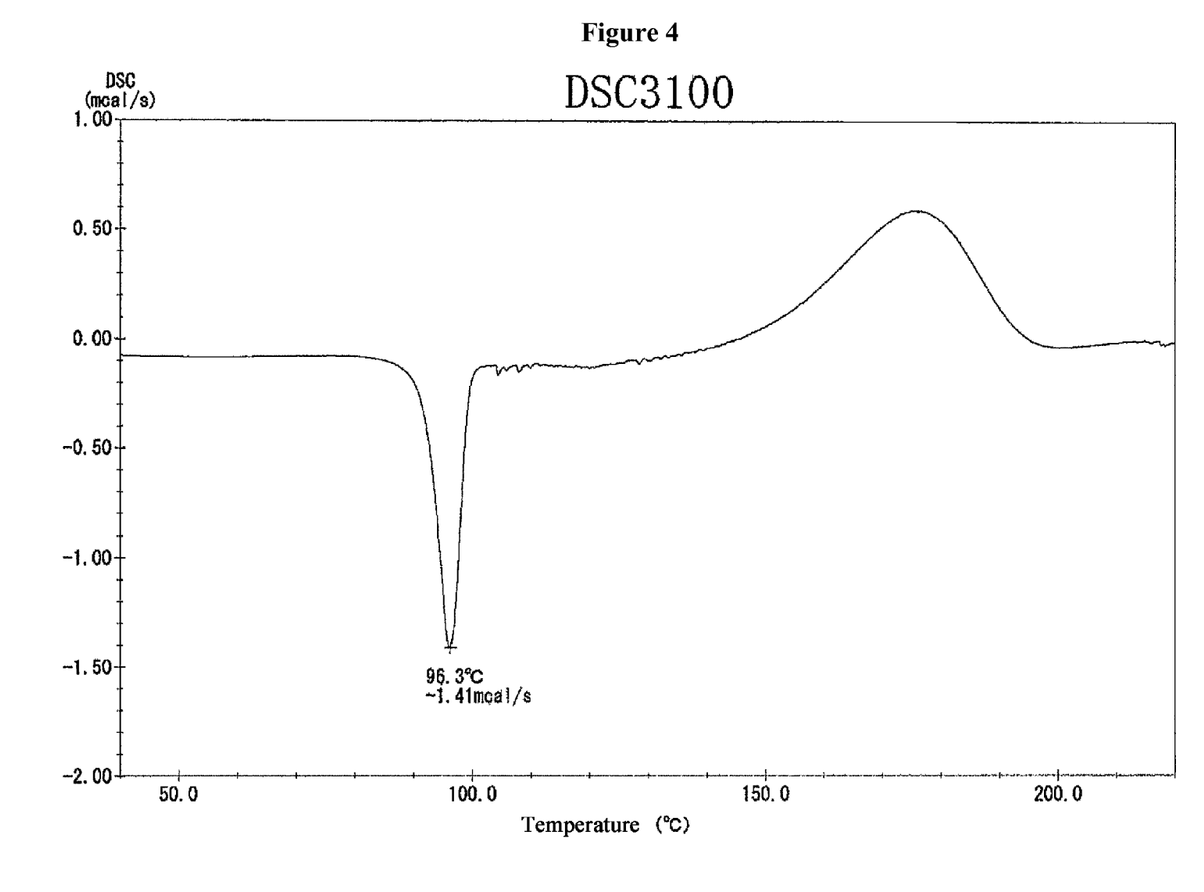
FIG. 4 shows a differential scanning calorimeter analysis (DSC) pattern of the crystals obtained in Example 1.
Figure 5:
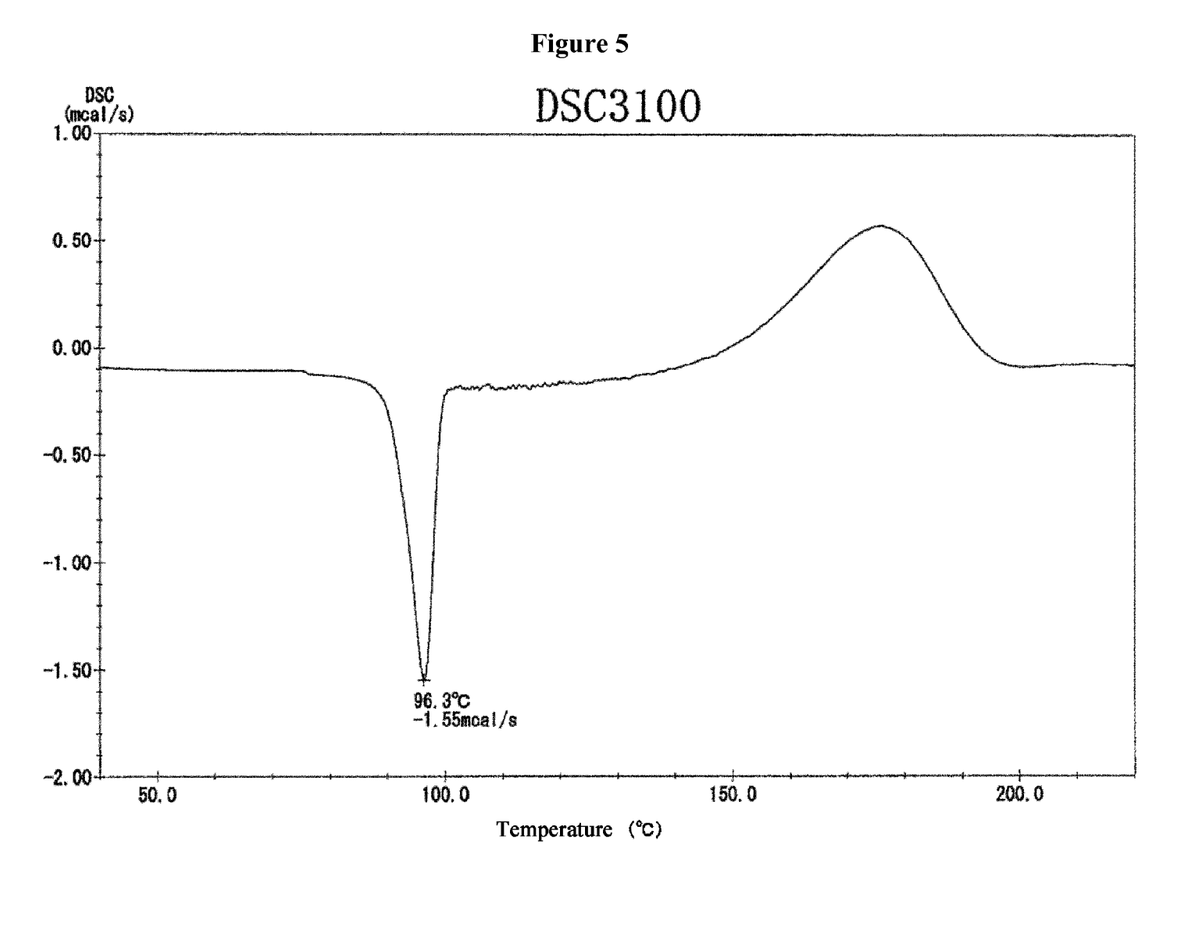
FIG. 5 shows a differential scanning calorimeter analysis (DSC) pattern of the crystals obtained in Example 2.

(3) The crystals according to (1) or (2), which exhibit a pattern equivalent to FIG. 4 or FIG. 5 in differential scanning calorimeter analysis of the crystals.

(4) The crystals according to any one of (1) to (3), which comprise 1 mol of acetone per 1 mol of trityl olmesartan medoxomil.

(5) A method for producing crystals according to any one of (1) to (4), which comprises a step of precipitating acetone solvate crystals of trityl olmesartan medoxomil from an acetone containing solution of trityl olmesartan medoxomil.

(6) The method according to (5), wherein the solvent of the acetone containing solution is acetone optionally containing water.

(7) The method according to (5), wherein the solvent of the acetone containing solution is acetone containing 20% (w/w) or less of water.

(8) The method according to (5), wherein the solvent of the acetone containing solution is acetone containing 10% (w/w) or less of water.

(9) The method according to (5), wherein the solvent of the acetone containing solution is acetone containing 5% (w/w) or less of water.

(10) The method according to (5), wherein the solvent of the acetone containing solution is acetone containing 2% (w/w) or less of water.

(11) The method according to (5), wherein the solvent of the acetone containing solution is acetone.

(12) The method according to any one of (5) to (11), wherein a seed crystal is added.

(13) A method for producing crystals according to any one of (1) to (4), which comprises the following steps:

(step 1) a step of tritylation and DMDO esterification of olmesartan in an acetone solvent optionally containing water; and (step 2) a step of precipitating acetone solvate crystals of trityl olmesartan medoxomil from the reaction mixture obtained in step 1.

(14) The method according to (13), wherein the water content in the acetone solvent during crystal precipitation is 20% (w/w) or less.

(15) The method according to (13), wherein the water content in the acetone solvent during crystal precipitation is 10% (w/w) or less.

(16) The method according to (13), wherein the water content in the acetone solvent during crystal precipitation is 5% (w/w) or less.

(17) The method according to (13), wherein the water content in the acetone solvent during crystal precipitation is 2% (w/w) or less.

(18) The method according to any one of (13) to (17), wherein acetone solvate crystals of trityl olmesartan medoxomil are precipitated by cooling the reaction mixture obtained in step 1 at 0° C. to 25° C.

(19) The method according to any one of (13) to (17), wherein acetone solvate crystals of trityl olmesartan medoxomil are precipitated by cooling the reaction mixture obtained in step 1 at 15° C. to 25° C.

(20) The method according to any one of (13) to (19), wherein seed crystal is added.

(21) A method for producing olmesartan medoxomil, which comprises a step of removing the trityl group in crystals according to any one of (1) to (4).

(22) The method according to (21), which comprises the step described in (5).

(23) The method according to (21), which comprises step 1 and step 2 described in (13).

In the present invention, olmesartan, trityl olmesartan medoxomil, olmesartan medoxomil, olmesartan medoxomil dehydrate, trityl halide and DMDO halide represent compounds represented by the structural formulas described in the figure above, respectively. In the structural formulas of trityl halide and DMDO halide, each X independently represents a halogen atom such as chloro, bromo and iodo. Tr represents triphenylmethyl. DMDO represents the portion in which X is eliminated in the structural formula of DMDO halide. Trityl olmesartan represents a compound represented by the structural formula described in the figure below.

Trityl olmesartan

The compound names of olmesartan, trityl olmesartan medoxomil, olmesartan medoxomil and DMDO chloride (DMDO-Cl) are indicated in Examples described below, and are as follows.

Olmesartan: 4-(1-Hydroxy-1-methylethyl)-2-propyl-1-[[2'-[1H-tetrazol-5-yl]biphenyl-4-yl]methyl]imidazole-5-carboxylic acid;

Trityl olmesartan medoxomil: (5-Methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate;

Olmesartan medoxomil: (5-Methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate;

DMDO chloride (DMDO-Cl): 4-Chloromethyl-5-methyl-1, 3-dioxol-2-one.

The crystal(s) of the present invention is a solid whose internal structure three-dimensionally consists of regularly repeating constituent atoms (or atomic groups), and is distinguished from an amorphous solid without such a regular internal structure.

In crystals of the same compound, plural crystals having different internal structures and physicochemical properties (polymorphic crystals) may be formed depending on the crystallization conditions, and the crystals of the present invention may be any of such polymorphic crystals or a mixture of two or more polymorphic crystals.

The form of the crystals of the present invention may be a form which exhibits the pattern shown in FIG. 1 or FIG. 2 in X-ray crystal diffraction, or the pattern shown in FIG. 4 or FIG. 5 in differential scanning calorimeter analysis, and there is no limitation to these so long as they are acetone solvate crystals of trityl olmesartan medoxomil.

Effect of the Invention

The novel solvate crystals provided by the present invention can be easily handled and are useful as synthetic intermediates of olmesartan medoxomil.

DETAILED DESCRIPTION

Olmesartan as the starting material used in the production method of the present invention can be easily produced according to the method described in Japanese Examined Patent Publication No. Hei 7-121918 (Japanese Patent No. 2082519; U.S. Pat. No. 5,616,599) or the like.

Acetone solvate crystals of trityl olmesartan medoxomil in the present invention may be obtained by the following steps, for example.

(Tritylation Step)

This step is a step in which trityl olmesartan is produced by reacting olmesartan with a trityl halide in an acetone solvent in the presence of a base.

Trityl chloride or trityl bromide is usually used as trityl halide, and trityl chloride is preferable.

The reaction solvent is usually used in a 5 to 20 (v/w)-fold amount to olmesartan, and this is not particularly restrictive.

The base used is not particularly restricted, and an amine such as triethylamine, diisopropylethylamine, pyridine or 1,8-diazabicyclo[5,4,0]-7-undecene (DBU) is preferably used, and DBU is most preferable.

The reaction temperature is not particularly restricted, and the reaction is usually carried out at a temperature in the range of 0° C. to the boiling point of the solvent, and preferably at 20 to 60° C.

Upon completion of the reaction, the trityl olmesartan may be isolated by a method usually used in the field of synthetic organic chemistry, and in the present invention, the reaction mixture is preferably used directly in the following DMDO esterification step without isolation of the trityl olmesartan.

(DMDO Esterification Step)

This step is a step in which trityl olmesartan medoxomil is produced by reacting trityl olmesartan with a DMDO halide in an acetone solvent in the presence of a base.

DMDO chloride or DMDO bromide is usually used as the DMDO halide, and DMDO chloride is preferable.

The base used is the same as in the tritylation step above, and DBU is preferable.

The reaction temperature is not particularly restricted, and the reaction is usually carried out at a temperature in the range of 0° C. to the boiling point of the solvent, and preferably at 20 to 60° C.

In the present invention, it is preferable for water to be present in the reaction mixture in the tritylation and DMDO esterification steps described above.

The amount of water present in the reaction mixture can be usually adjusted by adding water to the reaction mixture. Water may be added at once in the tritylation step, and may also be added separately in the tritylation step and in the DMDO esterification step.

The amount of water added to the reaction mixture is preferably adjusted in consideration of the water content in the starting materials, reaction reagents and solvent, so as to make the amount of water present in the reaction mixture as a whole (the water content in the reaction mixture) appropriate.

The water content in the reaction mixture is defined as the proportion (w/w) % [or % (w/w)] of the total water content (weight) to the total weight of the whole reaction mixture, by totaling the water contents in the starting materials, reaction reagents and reaction solvent.

The water contents in the starting materials, reaction reagents and reaction solvent may be measured using a Karl Fischer moisture measuring apparatus. For commercially available reagents or solvents, these may be calculated using the measured values or standard values described in the manufacturer's package insert.

The lower limit of the water content in the reaction mixture is usually 0.3 (w/w) % or more, and preferably 0.4 (w/w) % or more and most preferably 0.5 (w/w) % or more.

The upper limit of it is usually 3 (w/w) % or less, and preferably 2 (w/w) % or less and most preferably 1.5 (w/w) % or less.

When the water content in the reaction mixture increases, the efficiency of the tritylation and DMDO esterification reactions is reduced, potentially lengthening the reaction time or lowering the reaction yield. Therefore, in consideration of both impurity content reduction and reaction efficiency, the water content in the reaction mixture is preferably 1.3 (w/w) % or less.

The water content in the reaction mixture, in consideration of both impurity content reduction and reaction efficiency, is usually from 0.3 to 3.0 (w/w) %, preferably from 0.3 to 1.5 (w/w) %, more preferably from 0.4 to 1.5 (w/w) % and most preferably from 0.4 to 1.3 (w/w) %.

The amount of water added to the reaction mixture can be more conveniently adjusted in terms of the proportion (w/w) % to olmesartan (weight) as the starting material.

Olmesartan as the starting material having a water content of from 0.3 to 0.5 (w/w) % is usually used. DBU having a water content of about 0.5% is usually used. Triphenylmethyl chloride (TPC) and DMDO chloride usually contain essentially no water. When acetone is used as a solvent, that having a water content of about 0.2% is usually used. Acetone in a 5 to 20 (v/w)-fold amount to olmesartan is usually used.

When the reaction is carried out under these conditions, the lower limit of the amount of added water is usually 1.0 (w/w) % or more, preferably 2.0 (w/w) % or more and most preferably 4.0 (w/w) % or more, to olmesartan. When the water content in the starting materials, reagents and solvent is more than described above, the amount of water added to the reaction mixture may be less.

The upper limit of it is usually 28 (w/w) % or less, and preferably 18 (w/w) % or less and most preferably 13 (w/w) % or less. In consideration of both impurity content reduction and reaction efficiency, it is preferably 10 (w/w) % or less.

The amount of water added to the reaction mixture is usually from 1.0 to 28 (w/w) %, preferably from 1.0 to 13 (w/w) %, more preferably from 2.0 to 13 (w/w) % and most preferably from 2.0 to 10 (w/w) %, to olmesartan.

(Crystal Precipitating Step)

Acetone solvate crystals of trityl olmesartan medoxomil may be precipitated by cooling the reaction product (reaction mixture) obtained in the step described above.

Acetone solvate crystals may be precipitated by concentrating or cooling the reaction mixture. It may be precipitated by adding a suitable amount of water to the reaction mixture.

The water content in the acetone solvent during crystal precipitation is usually 20% (w/w) or less, preferably 10% (w/w) or less, more preferably 5% (w/w) or less and most preferably 2% (w/w) or less.

The cooling temperature is preferably from 0 to 25° C., and more preferably from 15 to 25° C.

The cooling time is usually 10 minutes or more, and preferably 30 minutes or more. Cooling may also be carried out for 6 hours or more.

In order to precipitate the desired crystals efficiently, it is preferable to be stirred while cooling.

Precipitation of the crystals may be initiated naturally in the reactor, and it may also be initiated or promoted by addition of a seed crystal or addition of stimulation with ultraviolet waves or mechanical stimulation by rubbing of the reactor surface or the like. Addition of a seed crystal is preferable when the water content in the acetone solvent exceeds 5% (w/w).

Acetone solvate crystals of trityl olmesartan medoxomil in the present invention may be produced by the following method, independently of the production method comprising the steps described above.

Acetone solvate crystals of trityl olmesartan medoxomil may be produced by dissolving trityl olmesartan medoxomil or a salt thereof, produced by a known method, in an acetone containing solvent, adjusting the pH, concentrating the solution, mixing a poor solvent, adding a seed crystal, and the like, to bring acetone solvate of trityl olmesartan medoxomil to a supersaturated state in the resulting solution to be precipitated.

The acetone containing solvent is preferably acetone optionally containing water. Water may also be added after dissolving the trityl olmesartan medoxomil in acetone.

The amount of water in acetone is not particularly restricted so long as it is in such a range that precipitation of acetone solvate crystals is not inhibited, and is usually 20% (w/w) or less, preferably 10% (w/w) or less, more preferably 5% (w/w) or less and further preferably 2% (w/w) or less.

Precipitation of the crystals may be initiated naturally in the reactor, and it may also be initiated or promoted by addition of a seed crystal or addition of stimulation with ultraviolet waves or mechanical stimulation by rubbing of the reactor surface or the like. Addition of a seed crystal is preferable when the amount of water in the acetone solvent exceeds 5% (w/w).

Procedures such as pH adjustment, concentration and cooling may also be carried out if necessary.

For example, acetone solvate crystals may be precipitated by dissolving trityl olmesartan medoxomil in acetone, adding a suitable amount of water to adjust the water content, and concentrating or cooling the solution.

For example, acetone solvate crystals may be precipitated by dissolving trityl olmesartan medoxomil in acetone and concentrating or cooling the solution.

Also, for example, acetone solvate crystals may be precipitated by dissolving trityl olmesartan medoxomil in acetone containing 20% (w/w) or less of water and concentrating or cooling the solution.

The precipitated crystals may be isolated by filtration, centrifugal separation or a gradient method, for example. The isolated crystals may be washed with an appropriate solvent as necessary.

For washing acetone solvate crystals, a solvent such as water, ethanol, isopropanol, acetone, ethyl acetate, toluene, acetonitrile, methyl acetate or ether may be used, and it is preferably water or acetone containing water.

The isolated crystals may be dried usually at a temperature of 10 to 100° C. and preferably 30 to 50° C., until the weight becomes essentially constant. Drying of the crystals may be carried out in the presence of a desiccant such as silica gel or calcium chloride, or under reduced pressure, as necessary.

The dried crystals may be allowed to absorb moisture until the weight becomes essentially constant, usually at a temperature of 10 to 30° C. and a relative humidity of 20% to 90%, and preferably at a temperature of 20 to 30° C. and a relative humidity of 50% to 80%.

Acetone solvate crystals of trityl olmesartan medoxomil in the present invention may exhibit a pattern equivalent to FIG. 1 or FIG. 2 in X-ray diffraction and that equivalent to FIG. 4 or FIG. 5 in differential scanning calorimeter analysis (DSC), respectively.

In the present invention, an equivalent pattern means a pattern which has no significant difference in the behavior of its main peaks.

Acetone solvate crystals of trityl olmesartan medoxomil in the present invention contain 1 mol of acetone per 1 mol of trityl olmesartan medoxomil in a dry form.

Acetone solvate crystals of trityl olmesartan medoxomil in the present invention may be converted to olmesartan medoxomil by a detritylation step (a step of removing a trityl group). The method for producing olmesartan medoxomil in the present invention comprises a step in which olmesartan medoxomil is produced by applying acetone solvate crystals of trityl olmesartan medoxomil obtained in the steps described above to a detritylation step. It is a feature of the present invention that novel acetone solvate crystals of trityl olmesartan medoxomil are used as the starting material in a detritylation step. The detritylation step may be the method described in, for example, Patent document 1, Patent document 2, Non-patent document 1 or Non-patent document 2, and it is not particularly restricted thereto.

By using acetone solvate crystals of trityl olmesartan medoxomil in the present invention as a synthetic intermediate, high-purity olmesartan medoxomil with reduced contents of impurities or analogs may be produced. The impurities or analogs whose contents are reduced include, for example, olmesartan and olmesartan medoxomil dehydrate.

When high-purity olmesartan medoxomil obtained in the present invention is used as a medicament, the dosage may be varied based on various conditions including patient symptoms, age, body weight or the like. The dosage differs depending on the symptoms, age, etc., and in oral administration, it may be 0.001 mg/kg (preferably 0.01 mg/kg) as the lower limit and 10 mg/kg (preferably 1 mg/kg) as the upper limit per day, with 1 to 6 times of administration a day depending on the symptoms.

When used for an adult human, it is usually administered orally at 5 to 40 mg dosage once a day, and most preferably a tablet comprising a dosage selected from 5 mg, 10 mg, 20 mg and 40 mg is administered orally once a day.

A medicament comprising high-purity olmesartan medoxomil obtained in the present invention is effective for prophylaxis or treatment of hypertension or diseases derived from hypertension (more specifically, hypertension, cardiopathies [angina pectoris, myocardial infarction, arrhythmia, cardiac failure or cardiac hypertrophy], renal diseases [diabetic nephropathy, glomerular nephritis or renal sclerosis], cerebrovascular diseases [cerebral infarction or cerebral hemorrhage]) or the like.

EXAMPLES

The present invention is explained in more detail through the following Examples or the like, and the present invention is not limited thereto.

Example 1

(1) Tritylation and DMDO Esterification Reactions

After mixing 4-(1-hydroxy-1-methylethyl)-2-propyl-1-[[2'-[1H-tetrazol-5-yl]biphenyl-4-yl]methyl]imidazole-5-carboxylic acid (30 g), acetone (210 mL), 1,8-diazabicyclo [5,4,0]-7-undecene [DBU] (25.5 g) and triphenylmethyl chloride [TPC] (23.79 g), water (0.6 mL) was added and acetone (30 mL) was poured into the mixture, and the reaction mixture was stirred at 48 to 52° C. for 2 hours. Then, water (0.9 mL) was added and 4-chloromethyl-5-methyl-1,3-dioxol-2-one [DMDO-Cl] (18.5 g) was poured in, and the reaction mixture was stirred at 48 to 52° C. for 5 hours.

(2) Obtaining Crude Crystals of Trityl Olmesartan Medoxomil (Acetone Solvate Crystals)

After the reaction mixture was cooled to 20° C. to precipitate crystals, it was stirred at 15 to 25° C. for 40 minutes, and water (96 mL) was added dropwise over a period of 25 minutes, and then the reaction mixture was cooled to 0 to 5° C. and stirred for 30 minutes. The precipitated crystals were filtered out and washed with acetone-water (150 mL), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate (57.83 g) were obtained. These were then dried in vacuo at 60° C. for approximately 15 hours, and the dry acetone solvate crystals (57.50 g) were obtained.

Example 2

(1) Tritylation and DMDO Esterification Reactions

After mixing 4-(1-hydroxy-1-methylethyl)-2-propyl-1-[[2'-[1H-tetrazol-5-yl]biphenyl-4-yl]methyl]imidazole-5-carboxylic acid (700 kg), acetone (4630 L), 1,8-diazabicyclo [5,4,0]-7-undecene [DBU] (610 L) and triphenylmethyl chloride [TPC] (570 kg), water (14 L) was added and acetone (800 L) was poured into the mixture, and the reaction mixture was stirred at 48 to 52° C. for 2 hours. Then, water (20 L) was added and 4-chloromethyl-5-methyl-1,3-dioxol-2-one [DMDO-Cl] (315 L) was poured in, and the reaction mixture was stirred at 48 to 52° C. for 5 hours.

(2) Obtaining Crude Crystals of Trityl Olmesartan Medoxomil (Acetone Solvate Crystals)

After the reaction mixture was stirred overnight at 15 to 25° C. to precipitate crystals, water (2170 L) was added at 30° C., and the reaction mixture was cooled to 0 to 5° C. and stirred for 30 minutes. The precipitated crystals were filtered out and washed with acetone-water (3360 L), and wet crude acetone solvate crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate (1360 kg) were obtained.

Reference Example (1) Tritylation and DMDO Esterification Reactions

After mixing 4-(1-hydroxy-1-methylethyl)-2-propyl-1-[[2'-[1H-tetrazol-5-yl]biphenyl-4-yl]methyl]imidazole-5-carboxylic acid (700 kg), acetone (5300 L), 1,8-diazabicyclo [5,4,0]-7-undecene [DBU] (614 L) and triphenylmethyl chloride [TPC] (570 kg), acetone (140 L) was poured into the mixture and water (14 L) was added, and the reaction mixture was stirred at 30 to 45° C. for 1 hour and then at 48 to 54° C. for 2 hours. Then, water (20 L) was added at 10 to 20° C. and 4-chloromethyl-5-methyl-1,3-dioxol-2-one [DMDO-Cl] (316 L) was poured in, and the reaction mixture was stirred at 28 to 32° C. for 3 hours and then at 48 to 52° C. for 3.5 hours.

(2) Obtaining Crude Crystals of Trityl Olmesartan Medoxomil

After the reaction mixture was stirred overnight at 28 to 32° C., water (2240 L) was added at 25° C., and the reaction mixture was stirred at 15 to 25° C. to precipitate crystals and then cooled to 0 to 5° C. and stirred for 30 minutes. The precipitated crystals were filtered out and washed with acetone-water (3420 L), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate (1460 kg) were obtained.

Example 3

X-Ray Crystal Diffraction of Acetone Solvate Crystals

Figure 3:
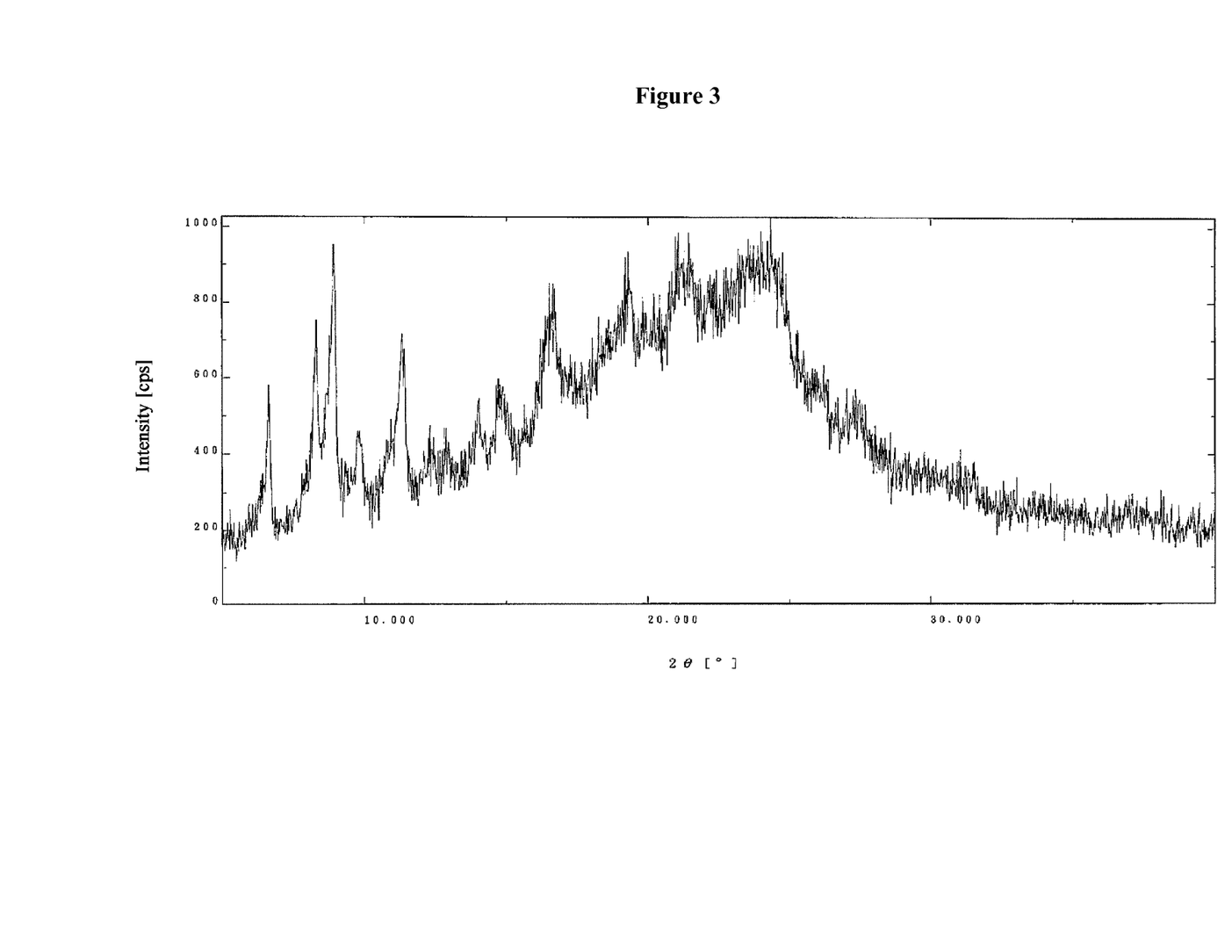
FIG. 3 shows an X-ray crystal diffraction pattern of the crystals obtained in Reference Example.

The dry crystals obtained in Example 1, and dry crystals obtained by drying the wet crystals obtained in Example 2 and Reference Example in vacuo at 60° C. for approximately 15 hours, were measured by powder X-ray crystal diffraction.

FIG. 1 shows a X-ray crystal diffraction pattern of the crystals obtained in Example 1.

FIG. 2 shows a X-ray crystal diffraction pattern of the crystals obtained in Example 2.

FIG. 3 shows a X-ray crystal diffraction pattern of the crystals obtained in Reference Example.

Example 4

Figure 6:
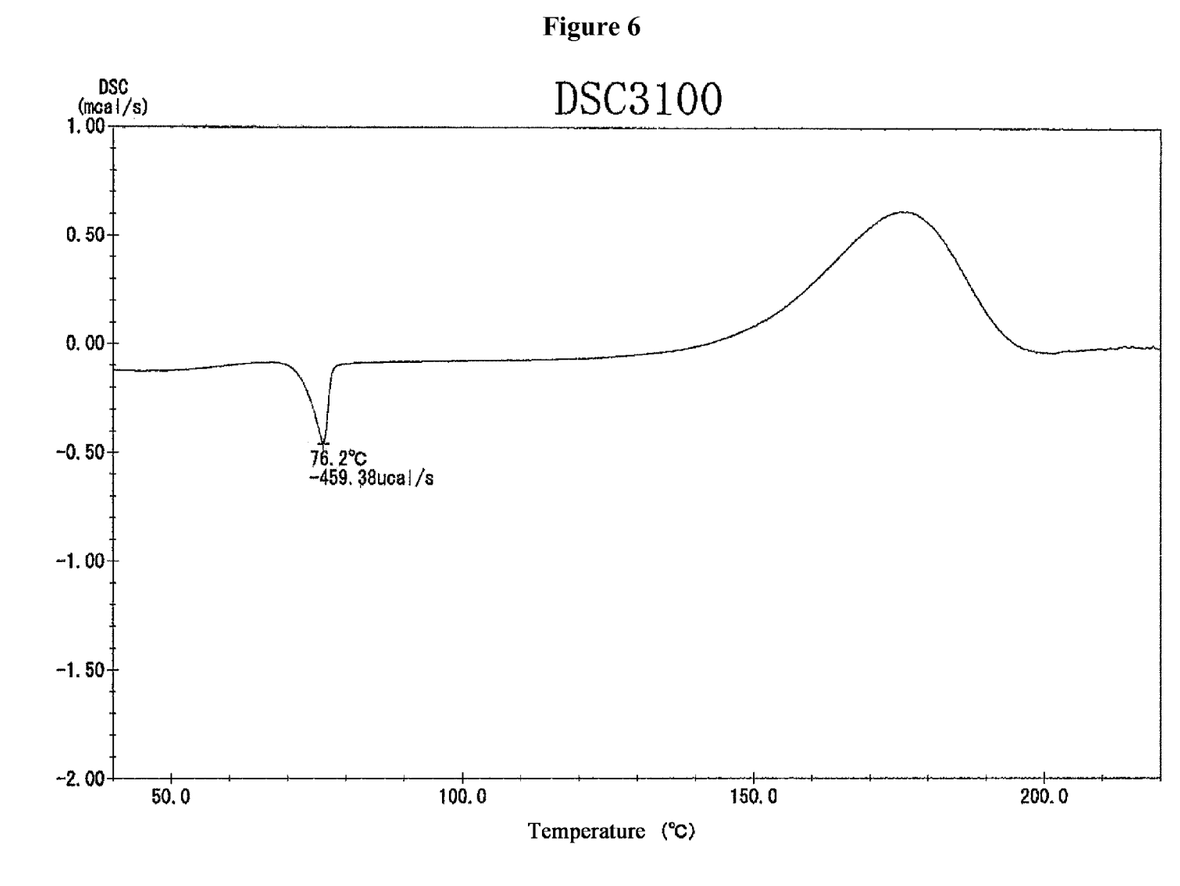
FIG. 6 shows a differential scanning calorimeter analysis (DSC) pattern of the crystals obtained in Reference Example.

Differential Scanning Calorimeter Analysis (DSC) of Acetone Solvate Crystals The dry crystals obtained in Example 1, and dry crystals obtained by drying the wet crystals obtained in Example 2 and Reference Example in vacuo at 60° C. for approximately 15 hours, were applied to differential scanning calorimeter analysis (DSC).

FIG. 4 shows a differential scanning calorimeter analysis (DSC) pattern of the crystals obtained in Example 1.

FIG. 5 shows a differential scanning calorimeter analysis (DSC) pattern of the crystals obtained in Example 2.

FIG. 6 shows a differential scanning calorimeter analysis (DSC) pattern of the crystals obtained in Reference Example.

Example 5

Acetone Content in Acetone Solvate Crystals

Acetone content in the dry crystals obtained in Example 1, and dry crystals obtained by drying the wet crystals obtained in Example 2 and Reference Example in vacuo at 60° C. for approximately 15 hours, were measured under the following conditions.

(Test Conditions)

Detector: Hydrogen ionization detector

Column: The inner wall of a fused silica tube with an inner diameter of 0.53 mm and a length of 30 m was coated with polyethylene glycol for gas chromatography with a thickness of 1 μm.

Column temperature: 50° C. for 5 minutes, followed by raising to 180° C. at 10° C./min, and holding at 180° C. for 5 minutes.

Inlet temperature: Constant temperature near 200° C.

Detector temperature: Constant temperature near 200° C.

Carrier gas: Helium

Flow rate: Adjusted so that retention time of acetone is approximately 2.5 minutes.

Split ratio: 1:5

Operating conditions of head space sample injector

Vial internal equilibrium temperature: constant temperature near 80° C.

Vial internal equilibrium time: 30 minutes

Injection line temperature: Constant temperature near 90° C.

Carrier gas: Helium

Sample injection amount: 1 mL

Figure 7:
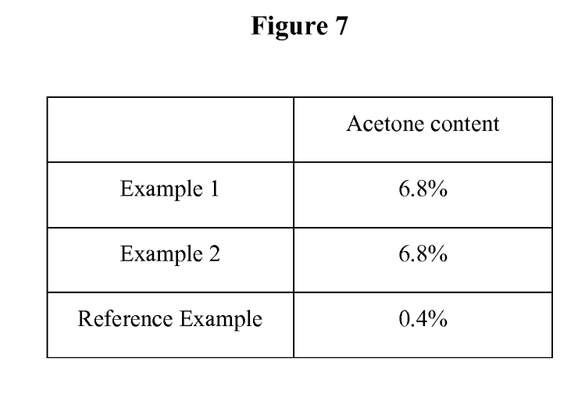
FIG. 7 shows the acetone contents in the crystals obtained in Examples 1 and 2 and Reference Example.

As shown in FIG. 7, the acetone contents in the crystals obtained in Example 1 and Example 2 were 6.8%. Since trityl olmesartan medoxomil has a molecular weight of 800.91 and acetone has a molecular weight of 58.08, and 1 mol of the latter corresponds to 6.76%, this suggested that 1 mol of acetone per 1 mol of trityl olmesartan medoxomil was present in the crystals obtained in Example 1 and Example 2.

In contrast, the acetone content in the crystals obtained in Reference Example was 0.4%.

The invention claimed is:

1. Acetone solvate crystals of trityl olmesartan medoxomil.

2. The crystals according to claim 1, which exhibit a pattern equivalent to FIG. 1 or FIG. 2 in powder X-ray crystal diffraction.

3. The crystals according to claim 1, which exhibit a pattern equivalent to FIG. 4 or FIG. 5 in differential scanning calorimeter analysis of the crystals.

4. The crystals according to claim 1, which comprise 1 mol of acetone per 1 mol of trityl olmesartan medoxomil.

5. A method for producing crystals according to claim 1, which comprises a step of precipitating acetone solvate crystals of trityl olmesartan medoxomil from an acetone containing solution of trityl olmesartan medoxomil.

6. The method according to claim 5, wherein the solvent of the acetone containing solution is acetone optionally containing water.

7. The method according to claim 5, wherein the solvent of the acetone containing solution is acetone containing 20% (w/w) or less of water.

8. The method according to claim 5, wherein the solvent of the acetone containing solution is acetone containing 10% (w/w) or less of water.

9. The method according to claim 5, wherein the solvent of the acetone containing solution is acetone containing 5% (w/w) or less of water.

10. The method according to claim 5, wherein the solvent of the acetone containing solution is acetone containing 2% (w/w) or less of water.

11. The method according to claim 5, wherein the solvent of the acetone containing solution is acetone.

12. The method according to claim 5, wherein a seed crystal is added.

13. A method for producing crystals according to claim 1, which comprises the following steps:
(step 1) a step of tritylation and DMDO esterification of olmesartan in an acetone solvent optionally containing water; and
(step 2) a step of precipitating acetone solvate crystals of trityl olmesartan medoxomil from the reaction mixture obtained in step 1.

14. The method according to claim 13, wherein the water content in the acetone solvent during crystal precipitation is 20% (w/w) or less.

15. The method according to claim 13, wherein the water content in the acetone solvent during crystal precipitation is 10% (w/w) or less.

16. The method according to claim 13, wherein the water content in the acetone solvent during crystal precipitation is 5% (w/w) or less.

17. The method according to claim 13, wherein the water content in the acetone solvent during crystal precipitation is 2% (w/w) or less.

18. The method according to claim 13, wherein acetone solvate crystals of trityl olmesartan medoxomil are precipitated by cooling the reaction mixture obtained in step 1 at 0° C. to 25° C.

19. The method according to claim 13, wherein acetone solvate crystals of trityl olmesartan medoxomil are precipitated by cooling the reaction mixture obtained in step 1 at 15° C. to 25° C.

20. The method according to claim 13, wherein a seed crystal is added.

21. A method for producing olmesartan medoxomil, which comprises a step of removing the trityl group in crystals according to claim 1.

22. The method according to claim 21, which comprises the step described in claim 5.

23. The method according to claim 21, which comprises step 1 and step 2 described in claim 13.

* * * * *